US006424597B1

(12) United States Patent
Bolomey et al.

(10) Patent No.: US 6,424,597 B1
(45) Date of Patent: Jul. 23, 2002

(54) MULTIELEMENTS ULTRASONIC CONTACT TRANSDUCER

(75) Inventors: Jean-Charles Bolomey, Paris; Gérard Cattiaux, Chateaufort; Sylvain Chatillon, Nevilly sur Marne; Alain Joisel, Meudon; Marc Serre, Versailles, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/600,987

(22) PCT Filed: Nov. 25, 1999

(86) PCT No.: PCT/FR99/02912
§ 371 (c)(1),
(2), (4) Date: Jul. 25, 2000

(87) PCT Pub. No.: WO00/33292
PCT Pub. Date: Jun. 8, 2000

(30) Foreign Application Priority Data

Nov. 27, 1998 (FR) .............................................. 98 14971

(51) Int. Cl.$^7$ ........................ G01N 29/24; H04R 17/00
(52) U.S. Cl. ........................ 367/138; 367/155; 367/128
(58) Field of Search ................................. 367/119, 138, 367/153, 155, 128; 310/334

(56) References Cited

U.S. PATENT DOCUMENTS

| 4,703,443 A | 10/1987 | Moriyasu |
| 5,680,863 A | 10/1997 | Hossack et al. |
| 5,913,825 A | 6/1999 | Watanabe et al. |
| 5,920,285 A | * 7/1999 | Benjamin .................... 342/368 |

FOREIGN PATENT DOCUMENTS

EP 0 312 481 4/1989

OTHER PUBLICATIONS

Powell et al., "A flexible Ultrasonic Array Incorporating a Platlet Composite Transmitte—Theory and Experiment", 1993 Ultrasonics Symposium, pp. 687–690.*

J. Ch. Bolomey, La Methode de Diffusion Modulee Une Approche Au Releve des Cartes de Champs Microondes en Temps Reel, L'onde Electrique, May 1982, vol. 62, No. 5, pp. 73–77.

WO 94/13411, Ultrasonic Transducer, Publication Date Jun. 23, 1994.

Metalscan, Systeme numerique de controle par ultrasons sinus O.L. 0° MTS (control manual), Jun. 1995, pp. 1–10.

D. J. Powell et al., Flexible Ultrasonic Transducer Arrays fro Nondestructive Evaluation Applications–Part I: The Theoretical Modeling Approach, IEEE Transactions on Ultrasonics, Ferroelectrics, and Frequecy Control, May 1996, vol. 43, No. 3, pp. 385–392.

D.J. Powell et al., Flexible Ultrasonic Transducer Arrays for Nondestructive Evaluation Application–Part II: Performance Assessment of Different Array Configurations, IEEE Transactions on Ultrasonics, Ferroelectrics, and Frequency Control, May 1996, vol. 43, No. 3, pp. 393–402.

* cited by examiner

*Primary Examiner*—Ian J. Lobo
(74) *Attorney, Agent, or Firm*—Pearne & Gordon LLP

(57) ABSTRACT

This transducer comprises means (16 to 24, 56 to 60) for determining the respective positions of ultrasound emitting elements (6) with respect to an object to be inspected (8) during displacement of the transducer. Means (62) generate pulses exciting emitting elements, and create delay laws starting from determined positions enabling emitting elements to generate a focused ultrasonic beam (F), and apply these laws to the excitation pulses. Ultrasound receiving elements provide signals used to form images related to the object. Application to medicine and nondestructive testing.

10 Claims, 4 Drawing Sheets

MULTIELEMENTS ULTRASONIC CONTACT TRANSDUCER

DESCRIPTION

1. Technical Field

Figure 1:
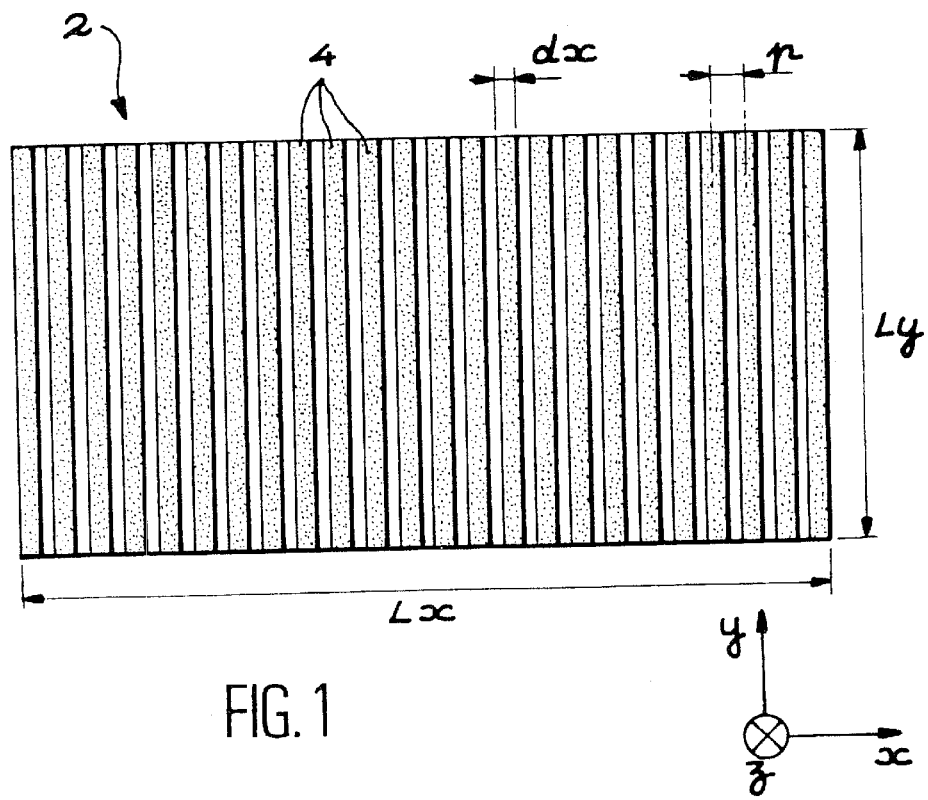

This invention relates to an ultrasonic contact transducer with multiple elements.

It is particularly applicable to medicine and nondestructive destructive testing of mechanical parts, and particularly parts with a complex shape or irregular surface condition, for example due to grinding.

2. State of Prior Art

In many industrial fields, and particularly in the case of nuclear power stations, testing by an ultrasonic contact transducer plays an important role in material inspection.

This technique consists of moving this ultrasonic transducer directly into contact with a part to be inspected. For each of its positions, the transducer emits ultrasonic pulses and records echoes reflected by the structure and possibly part defects.

However, many geometric aspects make the use of ultrasounds difficult; restricted access (particularly for connections), variable surface conditions and profile variations. Transducers used during these inspections are conventional transducers that cannot optimize the examination.

For example, depending on the areas, sensitivity variations can be observed caused by bad contact between the transducer and the inspected part, or inaccurate positioning may occur due to incorrect orientation of the transducer pressed in contact with the part, or a weld may be only partially covered when the transducer is prevented from moving by the surface configuration.

Therefore, many difficulties are observed during inspections carried out on parts with complex configurations. They illustrate the limits to the performances of conventional ultrasonic contact transducers:

1) Variation of the Thickness of the Coupling Layer

Contact is not optimal when the ultrasonic transducer passes over an area with a nonconforming surface condition or with configuration variations. Thus, the coupling layer located between the surface of the test piece being inspected and the emitting surface of the transducer has a variable thickness. Therefore the delay due to passing through this layer is different for ultrasonic waves emitted from different points on the transducer surface.

Furthermore, complex interference phenomena between the different successively reflected waves occur in this layer. The result is a deterioration of the ultrasonic beam resulting in a loss of sensitivity of the inspection. The capacity of the transducer to detect defects is thus limited.

2) Incorrect Transducer Orientations

The orientation of a transducer pressed on a test piece while being used to make an inspection of a test piece with profile variations, varies during the inspection. Thus, the direction of propagation of the ultrasonic wave in the test piece cannot be controlled since it changes as the transducer is displaced along the profile.

During an inspection carried out in manual mode, the operator cannot make the displacement along a perfectly straight line, which causes another disorientation of the transmitted ultrasonic beam. Information about the position of the defect in the test piece is then lost since the direction of propagation of the beam in this test piece is unknown.

3) Restricted Access

In some cases, the configuration of a part to be inspected makes it impossible to move the transducer along the full length of this part. The area to be inspected can only be partially covered.

We will now examine known solutions for solving these problems.

The ultrasonic beam is controlled by focusing the transmitted beam in the inspected part at a predetermined focusing depth and orientation.

The focusing principle consists of applying delays to the emitting surface such that contributions reach the required focal point in phase.

In the case of monolithic transducers, delays are physically distributed by applying a phase shifting lens formed on the emission surface. Therefore this type of system is fixed, and can only be satisfactory if there are no configuration variations on the part surface.

Dynamic shaping of the ultrasonic beam requires the use of transducers with multiple elements or multi-element transducers. Delays are electronically assigned to each element in the transducer, so that the characteristics of the ultrasonic beam generated by a single element can be modified, and therefore the beam focus can be controlled, and at the same time deformations caused by surfaces with a variable configuration can be compensated.

1) Immersed Multi-element Transducers

An inspection of a part with a variable profile can be carried out using a multi-element transducer immersed in a coupling liquid, for example water. In this case, the transducer is no longer placed in direct contact with the part, but is separated from it by a sufficiently thick layer of water so that interference phenomena between the different ultrasonic waves successively reflected in the coupling layer (a water layer in the example considered) are strongly reduced.

During the inspection of a part with a complex geometry, the ultrasonic beam is focused by calculating the path in water and the material from which this part is made (for example steel) of ultrasonic waves limited by the different elements of the transducer to the focal point, for each position of the transducer.

This solution causes serious difficulties. The adapted delay law cannot be calculated without knowledge of the exact configuration of the part and the position and orientation of the transducer with respect to the part.

Furthermore, this inspection mode cannot always be used in an industrial environment. Local immersion of the part may be difficult, particularly due to restricted access.

2) Multi-element Contact Transducers

Multi-element contact transducers are also used. However, degradations to the transmitted field due to an unsuitable contact are present during the inspection of parts with complex configurations.

Algorithmic techniques have been developed to compensate for this degradation, but they are not very satisfactory because they require that known defects should be present in the part.

One recently developed solution consists of using a multi-element contact transducer with a deformable emitting surface to adapt to the exact surface of the part. In this case contact is optimal, the coupling layer between the emitting surface and the inspected part remains sufficiently thin and uniform to not disturb transmission of the wave.

One particular transducer is obtained from rigid piezoelectric wafers (made of ceramic) embedded in a flexible substrate that is passive to ultrasounds and is described in the following documents:

D. J. Powell, and G. Hayward "Flexible ultrasonic transducer arrays for Nondestructive evaluation applications PART I: The theoretical modeling approach", IEEE transactions on ultrasonics, ferroelectrics, and frequency control, vol. 43, No. 3, May 1996, pages 385 to 392;

D. J. Powell and G. Hayward, "Flexible ultrasonic transducer arrays for nondestructive evaluation applications PART II: Performance assessment of different array configurations", IEEE transactions on ultrasonic, ferroelectrics, and frequency control, vol. 43, No. 3, May 1996, pages 393–402; and Internal patent application WO 94/13411, international publication date: Jun. 23, 1994 for "Ultrasonic transducer", invented by G. Hayward and D. J. Powell.

However in this case, control of the transmitted ultrasonic beam in order to optimize characterization of defects requires exact knowledge of the geometry of the inspected part and the position and orientation of the transducer with respect to this part.

DESCRIPTION OF THE INVENTION

This invention is designed to improve the performance of the ultrasound inspection of a part with a complex geometry (mechanical part or even part of the human body) in order to better detect, localize and characterize defects in this object.

Improvement of this performance requires control of the ultrasonic beam transmitted in the object, particularly concerning the focusing depth and orientation of this beam.

More precisely, the purpose of this invention is an ultrasonic contact transducer with multiple elements, each element being an ultrasound transmitter and/or receiver, the transducer being designed to be moved with respect to an object to be inspected and with a deformable emitting surface designed to come into contact with the surface of this object, and from which ultrasounds are emitted to the object, control means being provided to generate excitation pulses for emitting elements, this transducer being characterized in that it comprises means of determining the positions of each of the ultrasound emitting elements with respect to the object as the transducer is being moved, processing means being provided to:

generate delay laws, starting from the position thus determined, such that emitting elements can generate a focused ultrasonic beam with characteristics that are controlled with respect to the object, and apply these delay laws to excitation pulses, the ultrasound receiving elements being designed to supply signals for the formation of images related to the object.

With this invention, it is no longer necessary to know the exact configuration of the object since it is measured by the transducer. The transducer is then capable of operating independently since it adapts to the real configuration of the inspection made by measurement, analysis and compensation of the deformation of the emitting surface of this transducer.

It can thus be considered that this transducer is "intelligent".

According to a first particular embodiment of the transducer according to the invention, multiple elements are formed from a flexible piezoelectric polymer strip and a network of adjacent electrodes obtained by metallic deposition.

According to a second particular embodiment, the multiple elements are rigid piezoelectric elements embedded in a flexible substrate that is passive with respect to ultrasounds.

According to a third particular embodiment, the multiple elements are rigid and assembled to each other mechanically in order to form an articulated structure.

According to a preferred embodiment of the transducer according to the invention, the means of determining the positions of each of the ultrasound emitting elements with respect to the object comprise:

first means designed to determine the positions of each of the emitting elements with respect to a non-deformable part of the transducer by measuring the deformation of the emitting surface, and to provide signals representative of the positions thus determined, second means designed to determine the position and orientation of this non-deformable part of the transducer with respect to the object and to supply representative signals of the position and orientation thus determined, and third means designed to supply the positions of each of the ultrasound emitting elements with respect to the object making use of the signals output by these first and second means.

Preferably, the first means comprise:

means of measuring the distance from separate and fixed parts of the non-deformable part of the transducer, from the backing of each element or a subassembly of ultrasound emitting elements, and auxiliary processing means designed to determine the position of each ultrasound emitting element, making use of the distances determined above.

According to a first particular embodiment of the invention, the distance measurement means comprise:

auxiliary ultrasound emitters fixed to the backings of the elements of the subassembly and designed to emit ultrasounds in sequence, auxiliary ultrasound receivers fixed to the non-deformable deformable part and designed to detect ultrasounds emitted by the auxiliary emitters, and means of measuring the distance of each auxiliary emitter from each receiver in a group of auxiliary receivers receiving higher intensity ultrasounds.

According to a second particular embodiment of the invention, the distance measurement means comprise:

a microwave source, a plurality of microwave antennas rigidly fixed to the non-deformable part, coupled to this source and designed to emit microwaves in sequence, and also to receive microwaves in sequence, microwave probes fixed to the different backings of elements of the sub-assembly and designed to scatter microwaves emitted by the antennas, these probes being fitted with non-linear devices to modulate the microwaves scattered by the probes, at different frequencies, and microwave reception means coupled to antennas and designed to measure the distance from each probe to each antenna by measuring the phase of the microwaves scattered by this probe and received by this antenna, these reception means also being designed to distinguish probes from each other by a synchronous detection at the different modulation frequencies.

Preferably, the auxiliary processing means are designed to determine a profile that best passes through the backings of the elements in the subassembly by an interpolation method, and to use this profile to determine the position of the emitting face of each ultrasound emitting element with respect to the non-deformable part of the transducer.

The second means may comprise an articulated mechanical arm fixed to the non-deformable part of the transducer.

BRIEF DESCRIPTION OT THE DRAWINGS

Figure 2:
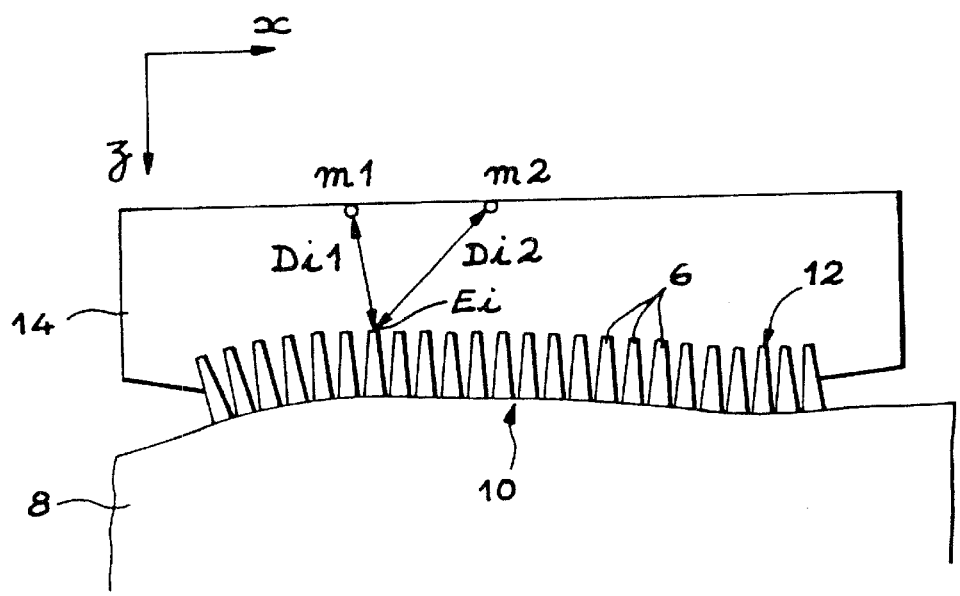
Figure 3:
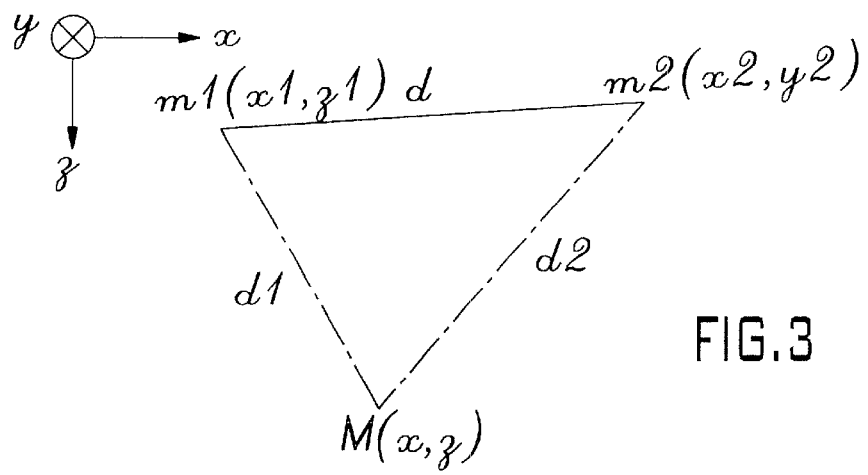
Figure 4:
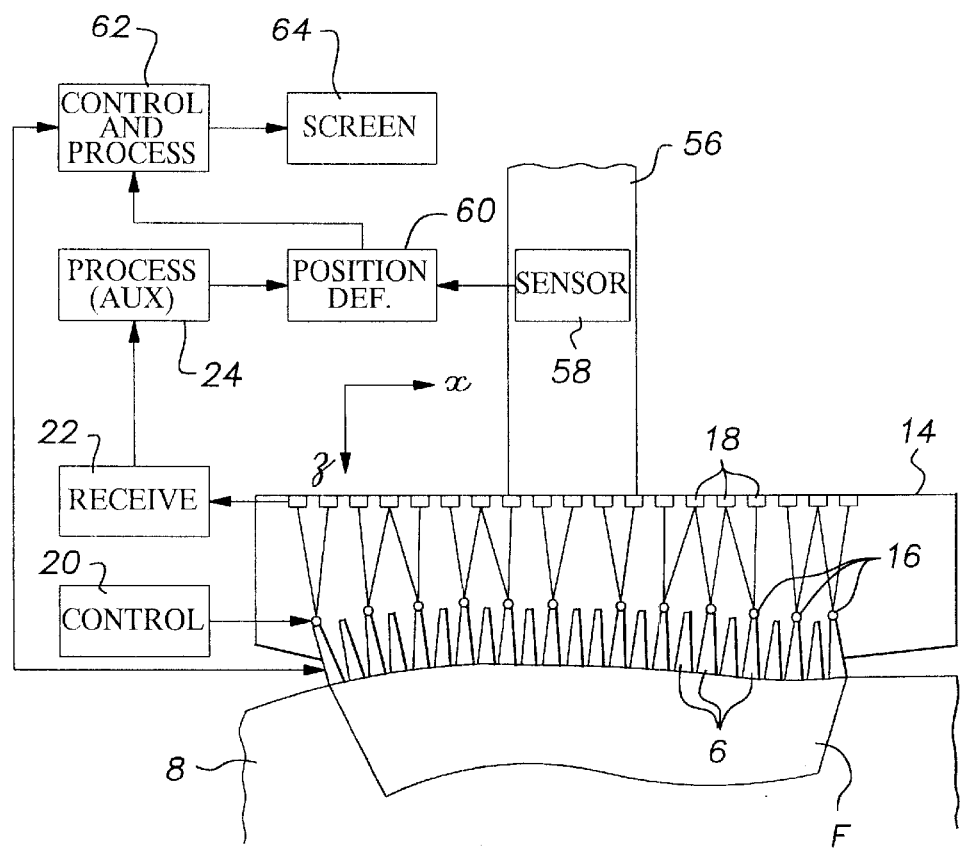
Figure 5:
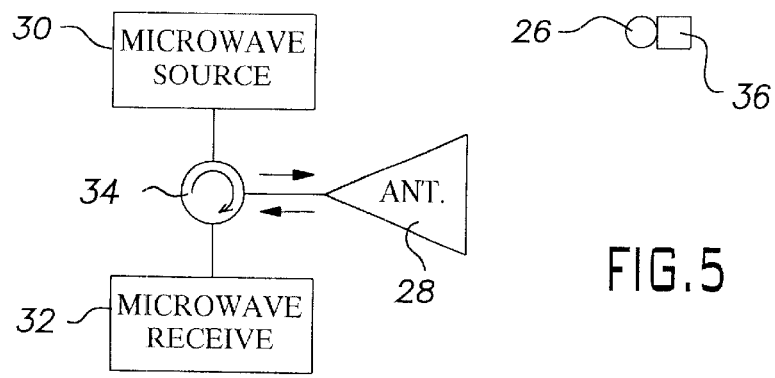
Figure 6:
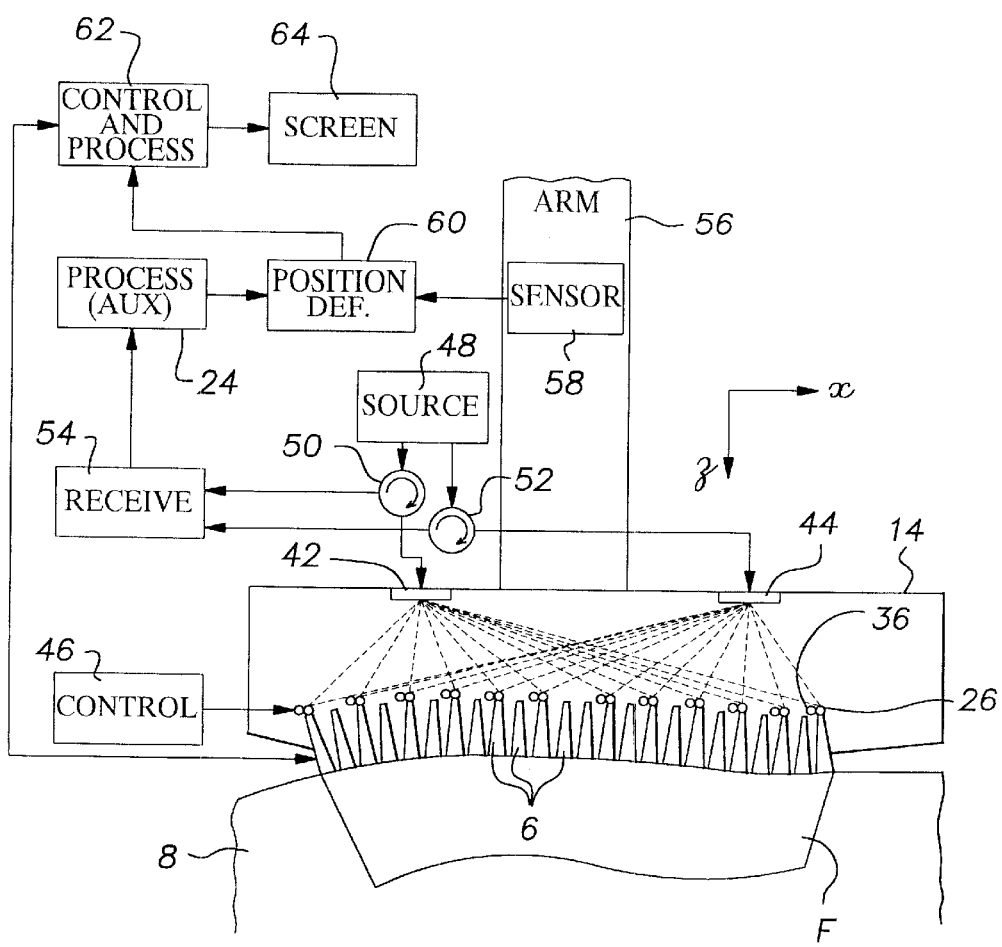
Figure 7:
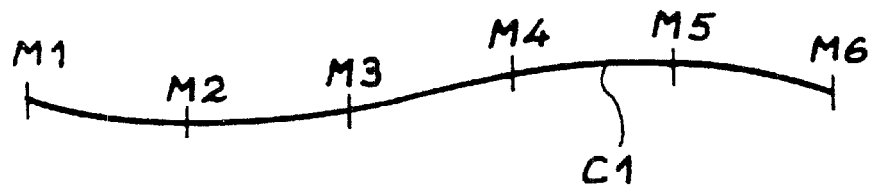
Figure 8:
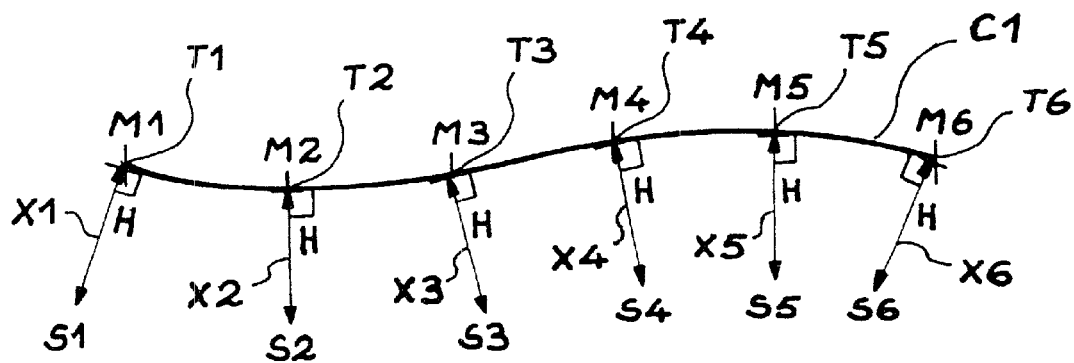
Figure 9:
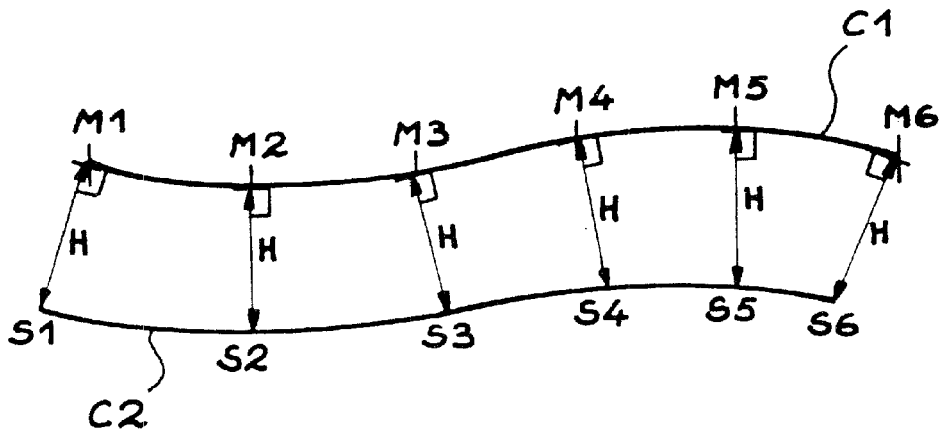

This invention will be better understood after reading the description of example embodiments given below, which is for information purposes only and is in no way restrictive, with reference to the attached drawings on which:

FIG. 1 is a diagrammatic view of the emitting surface of a linear module of ultrasound emitting/receiving elements, FIG. 2 diagrammatically illustrates an example deformation of the module in FIG. 1 over an arbitrary profile, FIG. 3 diagrammatically illustrates a triangulation principle that could be used in the invention, FIG. 4 is a diagrammatic view of a first particular embodiment of the transducer according to the invention, that uses auxiliary ultrasonic sensors, FIG. 5 diagrammatically illustrates the principle of a scattering method that can be used in the invention, FIG. 6 is a diagrammatic view of a second particular embodiment of the transducer according to the invention that uses microwave antennas, and FIGS. 7 to 9 diagrammatically illustrate three steps of an algorithm that can be used in the invention.

DETAILED DESCRIPTION OF PARTICULAR EMBODIMENTS

We will consider an ultrasonic transducer according to the invention. It is a transducer with multiple elements with a deformable emitting surface.

This emitting surface is designed to be moved over the surface of an object to be inspected, while being held in contact with this surface of the object.

Furthermore, according to the invention, this transducer comprises instrumentation for measuring the deformation of its emitting surface thus giving the position of the piezoelectric elements with respect to the rigid part of the transducer, and the position (3 coordinates) and orientation (3 components) of the rigid part of the transducer are measured with respect to the object.

For reasons of clarity, the following description applies to an ultrasonic transducer of the linear module type 2 (FIG. 1), which is subject to deformations only in the plane of incidence of the ultrasounds (x, z) in FIGS. 1 and 2.

The emitting surface of this transducer is broken down into independent elements 4 along only one direction, Ly, in FIG. 1.

The geometric parameters of this module 2 are shown in FIG. 1, in which the notations are as follows:

Lx=length in the plane of incidence (x, z)

Ly=width in the plane (y, z) perpendicular to the plane of incidence p=distance between the centers of two adjacent elements dx=width of an element.

The values of these parameters are determined depending on the application and the chosen acoustic characteristics, namely the central frequency and the signal band width.

This linear (in other words single-dimensional) transducer is capable of compensating for surface deformations in the plane of incidence (x, z) in FIG. 2.

This concept may be applied to the manufacture of matrix type ultrasonic transducers in which the breakdown of the emitting surface along the two directions x and y enables control of the ultrasonic beam in all directions in three-dimensional space.

Concerning the deformable nature of the transducer, several techniques are possible. They are defined by the nature of the piezoelectric material used.

Thus, the emitting surface may be composed of a flexible strip of piezoelectric polymer, typically PVDF, and a network of adjacent electrodes obtained by metallic deposition (see the documents written by Powell and Hayward, mentioned above)

Similarly, a technique described in the documents written by Powell and Hayward and the WO 94/13411 application, mentioned above, consists of using a se of rigid piezoelectric elements cast in a flexible substrate that is passive (in other words inert) with respect to ultrasounds.

Finally, a technique developed by the Metalscan company consists of using a set of rigid ultrasonic elements assembled to each other mechanically in order to obtain an articulated structure.

Regardless of the technique (existing or specially developed), it must be capable of obtaining local deformations with a very small radius of curvature (typically 15 mm to 20 mm) and may be transposed to the case of matrix type ultrasonic transducers.

FIG. 2 shows an example embodiment of this type of deformable linear multi-element module, as proposed by the Metalscan company.

The trapezoidal shape and dimensions of the ultrasound emitting-receiving elements 6 are designed to provide sufficient clearance to obtain the required deformation.

The inspected object in FIG. 2 is marked as reference 8. Each element has an active face 10 in contact with the surface of the object and a back surface 12 called the backing.

The transducer in FIG. 2 also comprises a nondeformable housing 14, in which the module with multiple elements 6 is fixed.

According to the invention, a system of measuring the deformation of the front face of this transducer (all active faces of elements are on the front face) is integrated in the transducer. This deformation is obtained starting from a specific instrumentation that will be described.

In the case of a single-dimensional module, the position of an element is determined by its two coordinates (x, z) measured in the transducer local coordinate system.

The technique chosen to obtain the coordinates (position) of each element in the transducer coordinate system consists of sampling the deformable surface by measuring the coordinates of a number of elements.

A polynomial interpolation technique is then applied in order to determine the coordinates of all elements.

The measurement used to obtain this sampling is based on the triangulation principle (FIG. 3).

In this case, the (x, z) coordinates of a point on the backing of an element M may be obtained starting from the measurement of two distances d1, d2 separating it from two distinct points m1, m2 with known coordinates (x1, z1), (x2, z2), these points m1 and m2 being separated from each other by a distance d.

Therefore, the instrumentation consists of a set of sensors used to measure the distances Di1, Di2 separating it from two perfectly known points m1, m2 on the transducer housing 14, for each element Ei (FIG. 2) chosen for sampling.

The distance sensors used must satisfy a number of requirements.

Firstly, the measurement of the distances is used to define delay laws to be applied to the module such that the resolution is sufficiently fine. A resolution of the order of $\lambda/10$ is chosen, where $\lambda$ is the wavelength of ultrasounds in the material being inspected.

For example, if the ultrasound frequency is 2 MHz and the material is steel, the resulting longitudinal wavelength is 2.95 mm. Therefore, the required resolution is of the order of 0.3 mm.

Furthermore, the complete instrumentation must be integrated into the transducer such that the elementary sensor dimension must be very small, of the order of 1 mm.

Finally, these sensors must be capable of processing a distance range of several millimeters.

Two sensor techniques satisfying these criteria were selected.

The first technique consists of using ultrasonic emitters and receivers (FIG. 4).

An auxiliary ultrasound emitter 16 is fixed to the backing of each element selected for sampling among elements 6, and a set of auxiliary ultrasound receivers 18 for which the positions are known, is fixed onto the inside face of the transducer housing 14 facing these emitters 16.

Each emitter 16 is dynamically associated with a pair of receivers 18 depending on the amplitude of the received signal.

The distance of an emitter 16 from each associated receiver 18 is estimated by measuring the flight time of the ultrasonic wave output from this emitter 16.

The use of different receivers 18, in other words different reference points on the housing, is imposed by the directivity of the ultrasonic waves.

The acoustic characteristics of emitters 16 and receivers 18 (particularly the central frequency and the band width) are chosen to give the required resolution.

With this technique, for obvious disturbance reasons, the emitters 16 must emit one after the other. Therefore, the positions of the different elements associated respectively with each of these emitters 16 must be obtained sequentially, and not simultaneously.

This is why a dynamic association was considered above; this means that when an emitter 16 is activated, the ultrasounds emitted by it are picked up by all receivers 18, and the two receivers out of all these receivers 18 that received higher intensity ultrasounds will be selected to associate these two receivers with the emitter considered 16.

FIG. 4 also shows means 20 of controlling the auxiliary emitters 16 in order to activate them one after the other, means 22 of receiving signals output by receivers 18, selecting two of these receivers to dynamically associate them with each emitter 16 as described above, and determine the distance of the backing of element 6 carrying this emitter with respect to each of these two associated receivers (and hence the position of the backing of this element 6 with respect to the housing 14), and auxiliary processing means 24 that, as will be seen later, determine the position of the active face of each of the elements 6 with respect to the housing.

The second technique is based on the modulated face principle applied to microwave antennas.

This technique is based on the principle of scattering and is described in the following document:

J. CH. Bomoley, La methode de diffusion modilee: une approche au releve des cartes de champs micro-ondes en temps reel" (The modulated scattering method, an approach to reading microwave field maps in real time) L'onde electrique, 1982, vol. 62, No. 5, pages 73–78.

It consists of measuring the disturbance of the electromagnetic field induced by the presence of a probe 26 (FIG. 5) in the field of a microwave antenna 28. Therefore the signal scattered by the probe is picked up at the antenna, this antenna being connected to a microwave source 30 and a microwave receiver 32 through a circulator 34.

This technique was originally intended for measurement of the field radiated by a microwave antenna, and conversely can be used to measure the distance separating the probe from the antenna. If the antenna radiation diagram is perfectly known, measuring the phase of the radiated field at the probe location is a means of identifying the distance separating this probe from the antenna.

In order to improve detection at the antenna, the signal scattered by the probe is modulated using a non-linear device 36, typically a diode.

This modulation technique also enables simultaneous use of different probes modulated at different frequencies, the distinction being made at the receiver by a simple synchronous detection at different modulation frequencies. It is thus possible to simultaneously measure the distance separating a set of probes in the same antenna.

The use of this technique is diagrammatically illustrated in FIG. 6, and therefore consists of placing a probe 26 modulated by non-linear device 36 on the backing of each of the elements 6 chosen for sampling, and fixing two microwave antennas 42 and 44 with known positions on this housing, on the inside face of the housing 14 facing the modulated probes 26.

Since these antennas cannot be used simultaneously, two acquisition sequences are necessary to obtain the distance separating each probe of an element in the same antenna.

Finally, note that the nature of the measured distance depends on the configuration of the radiation diagram for this antenna (this diagram typically being plane or spherical), which thus enables different instrumentation configurations.

FIG. 6 also shows:

control means 46 for controlling non-linear devices 36 that modulate the probes at different frequencies, the microwave source 48 that successively activates antennas 42 and 44 so that they successively emit microwaves which are connected to these antennas 42 and 44 respectively, through two circulators 50 and 52 respectively, the microwave receiver 54 that processes the signals that it receives in sequence from antennas through circulators 50 and 52, to determine the distance between the backing of each element 6 supporting a probe 26 and each antenna (and hence the position of the backing of this element 6 with respect to the housing 14), these distances being determined by measuring the phase of microwaves scattered by the probes, and the receiver being designed to make a distinction between probes by synchronous detection at different modulation frequencies, and auxiliary processing means 24, that determine the position of each of the elements with respect to the housing 14, as will be described below.

Therefore, the coordinates of all these elements 6 need to be obtained starting from sampling of the emitting surface of the module with multiple elements 6 (FIG. 4 or 6).

However, the measurement is made on the backing of an element, whereas the delay law is calculated from the position of the active face or emitting face of the element, in other words on the side of the emitting surface of the transducer.

Therefore, an algorithm was developed in order to determine this position. This algorithm contains three steps:

1) Using an interpolation, for example a cubic spline interpolation, we will determine the curve C1 that best matches the profile passing through the measurement points on the backing (see FIG. 7 in which six measurement points M1 to M6 are shown as an example).

2) We will assume that the centerline of each element (the centerline references are marked X1 to X6 in FIG. 8)

remains orthogonal to the local slope at the surface of the inspected part and to the local slope at the surface formed by the end of the backing of all elements (the references of the local slopes are T1 to T6).

Therefore starting from the backing profile, we measure the local derivative to determine the orientation of each measured element.

Starting from this orientation and the height H of each element, we thus obtain the coordinates of the corresponding point on the emitting surface (the references of these corresponding points in FIG. 8 are S1 to S6).

3) Finally, we apply a cubic "spline" type interpolation to the sampling points on the emitting surface.

The curve C2 thus obtained (FIG. 9) can be used to determine the position of the different elements in the coordinate system of the transducer, in other words with respect to the housing 14 of this transducer in the example considered.

We will now consider the instrumentation for measuring the position and orientation of the transducer in FIG. 4 or 6.

This instrumentation provided with the transducer must be capable of defining the position and orientation of the transducer as it moves in the fixed coordinate system of the object 8.

Several different sensors are capable of making this type of measurement.

An articulated mechanical arm 56 is used in the examples shown in FIGS. 4 and 6. The position and orientation of the arm during its displacement in contact with the object are measured or checked, depending on the nature of this arm (passive or active).

In the examples in FIGS. 4 and 6, this arm is fitted with various sensors 58 that locate the ultrasonic transducer in space and measure its orientation during its displacement with respect to the object 8.

One example of this type of arm is the mechanical part of the "sinus arm", marketed by the Metalscan Company (see the document "Publication by the METALSCAN Company, Grenoble, France, Reference SINU9506MTS, June 1995, 'Systeme numerique de controle par ultrasons', (Numerical control system by ultrasounds) SINUS O.L. O°MTS, pages 1–10").

FIGS. 4 and 6 also show means 60 that define the positions of the transducer with respect to object 8, as a function of the positions supplied by means 24 and the position and orientation supplied by the sensors 58.

They also show control and processing means 62 designed to:

generate excitation pulses for elements 6, define delay laws, starting from the positions thus determined, to enable elements 6 to generate a focused ultrasonic beam F, for which the characteristics are controlled with respect to the object 8, and apply these delay laws to excitation pulses.

The elements 6 then supply signals to means 62 also designed to supply images related to the object 8, making use of these signals. These images are displayed on a screen 64.

If a passive arm (without a sensor) is used, the user moves the transducer manually, and its position and orientation are measured by sensors 58, and supplied to means 60.

The arm may be replaced by other means, for example such as inertia sensors, also capable of supplying the position and orientation of the transducer.

Furthermore, the examples given use elements capable of emitting and receiving ultrasounds at the same time. An expert in the subject would be capable of adapting these examples to the case of transducers comprising elements designed solely to emit ultrasounds and other elements designed solely to receive ultrasounds.

These examples can also be adapted to a transducer emitting Lamb waves.

Furthermore, in these examples, the transducers used comprise a linear module of ultrasonic elements but the invention is not restricted to this type of transducers. An expert in the subject will be able to adapt the examples given to matrix transducers, for example of the type described in documents [1], [2] and [4].

In particular, each auxiliary ultrasound emitter (see FIG. 4) then needs to be dynamically associated with three receivers in a matrix of ultrasound receivers fixed to the housing 14, rather than two, or three microwave antennas instead of two can be used in the case of a matrix transducer adapted from that shown in FIG. 6.

What is claimed is:

1. Ultrasonic contact transducer with multiple elements (6), each element being an ultrasound emitting and/or receiving element, the transducer being designed to be moved with respect to an object to be inspected (8) and with a deformable emitting surface designed to come into contact with the surface of this object, and from which ultrasounds are emitted to the object, control means (62) being provided to generate excitation pulses for emitting elements, this transducer being characterized in that it comprises means (16, 18, 20, 22, 24, 56, 58, 60; 24, 38, 40, 42, 44, 46, 48, 50, 52, 54, 56, 58, 60) of determining the positions of each of the ultrasound emitting elements with respect to the object as the transducer is being moved, processing means being provided to:

generate delay laws, starting from the positions thus determined, such that emitting elements can generate a focused ultrasonic beam (F) with characteristics that are controlled with respect to the object, and apply these delay laws to excitation pulses, the ultrasound receiving elements being designed to supply signals for the formation of images related to the object.

2. Transducer according to claim 1, in which the multiple elements are formed from a flexible piezoelectric polymer strip and a network of adjacent electrodes obtained by metallic deposition.

3. Transducer according to claim 1, in which the multiple elements are rigid piezoelectric elements embedded in a flexible substrate that is passive with respect to ultrasounds.

4. Transducer according to claim 1, in which the multiple elements are rigid and assembled to each other mechanically in order to form an articulated structure.

5. Transducer according to claim 1, in which the means of determining the positions of each of the ultrasound emitting elements with respect to the object comprise:

first means (16, 18, 20, 22, 24; 24, 38, 40, 42, 44, 46, 48, 50, 52, 54) designed to determine the positions of each of the emitting elements with respect to a non-deformable part (14) of the transducer by measuring the deformation of the emitting surface, and to provide signals representative of the positions thus determined, second means (58, 60) designed to determine the position and orientation of this non-deformable part of the transducer with respect to the object and to supply representative signals of the position and orientation thus determined, and third means (60) designed to supply the positions of each of the ultrasound emitting elements with respect to the object making use of the signals output by these first and second means.

6. Transducer according to claim 5, in which the first means comprise:

means (16, 18, 20, 22; 38, 40, 42, 44, 46, 48, 50, 52, 54) of measuring the distance from separate and fixed points of the non-deformable part of the transducer, from the backing of each element of a subassembly of ultrasound emitting elements, and auxiliary processing means (24) designed to determine the position of each ultrasound emitting element, making use of the distances determined above.

7. Transducer according to claim 6, in which the distance measurement means comprise:

auxiliary ultrasound emitters (16) fixed to the backings of the elements of the subassembly and designed to emit ultrasounds in sequence, auxiliary ultrasound receivers (18) fixed to the non-deformable part and designed to detect ultrasounds emitted by the auxiliary emitters, and means (22) of measuring the distance of each auxiliary emitter from each receiver in a group of auxiliary receivers receiving higher intensity ultrasounds.

8. Transducer according to claim 6, in which the distance measurement means comprise:

a microwave source (48), a plurality of microwave antennas (42, 44) rigidly fixed to the non-deformable part, coupled to this source and designed to emit microwaves in sequence, and also to receive microwaves in sequence, microwave probes (38) respectively fixed to the different backings of elements of the sub-assembly and designed to scatter microwaves emitted by the antennas, these probes being respectively fitted with non-linear devices (40) designed to modulate the microwaves respectively scattered by the probes, at different frequencies, and microwave reception means (54) coupled to antennas and designed to measure the distance from each probe to each antenna by measuring the phase of the microwaves scattered by this probe and received by this antenna, these reception means also being designed to distinguish probes from each other by a synchronous detection at the different modulation frequencies.

9. Transducer according to claim 6, in which the auxiliary processing means (24) are designed to determine a profile that best passes through the backings of the elements in the sub-assembly by an interpolation method, and to use this profile to determine the position of the emitting face of each ultrasound emitting element with respect to the non-deformable part of the transducer.

10. Transducer according to claim 5, in which the second means comprise an articulated mechanical arm (56) fixed to the non-deformable part (14) of the transducer.

* * * * *

UNITED STATES PATENT AND TRADEMARK OFFICE
CERTIFICATE OF CORRECTION

PATENT NO. : 6,424,597 B1
DATED : July 23, 2002
INVENTOR(S) : Jean-Charles Bolomey et al.

It is certified that error appears in the above-identified patent and that said Letters Patent is hereby corrected as shown below:

<u>Title page,</u>
Item [56], References Cited, OTHER PUBLICATIONS, please delete "fro", and insert therefor -- for --; and please delete "Application", and insert therefor -- Applications --.

<u>Column 5,</u>
Line 1, please delete "OT", and insert therefor -- OF --.

<u>Column 6,</u>
Line 5, after "above)", please insert -- . --.

Signed and Sealed this

Tenth Day of December, 2002

JAMES E. ROGAN
*Director of the United States Patent and Trademark Office*